United States Patent
Liao et al.

(10) Patent No.: US 10,987,316 B2
(45) Date of Patent: Apr. 27, 2021

(54) COMPOSITIONS AND METHODS FOR TRANSDERMAL DELIVERY OF TERTIARY AMINE DRUGS

(71) Applicant: Noven Pharmaceuticals, Inc., Miami, FL (US)

(72) Inventors: Jun Liao, Miami, FL (US); Takito Shima, Miami, FL (US); Puchun Liu, Miami, FL (US); Steven Dinh, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 331 days.

(21) Appl. No.: 14/208,348

(22) Filed: Mar. 13, 2014

(65) Prior Publication Data

US 2014/0276478 A1 Sep. 18, 2014

Related U.S. Application Data

(60) Provisional application No. 61/793,120, filed on Mar. 15, 2013.

(51) Int. Cl.
| | | |
|---|---|---|
| *A61K 47/38* | (2006.01) | |
| *A61K 9/70* | (2006.01) | |
| *A61K 31/27* | (2006.01) | |
| *A61K 31/13* | (2006.01) | |

(52) U.S. Cl.
CPC .......... *A61K 9/7084* (2013.01); *A61K 9/7061* (2013.01); *A61K 31/13* (2013.01); *A61K 31/27* (2013.01)

(58) Field of Classification Search
CPC .... A61K 9/7084; A61K 31/27; A61K 9/7061; A61K 31/13
See application file for complete search history.

(56) References Cited

U.S. PATENT DOCUMENTS

| | | | |
|---|---|---|---|
| 5,234,957 A | 8/1993 | Mantelle | |
| 5,332,576 A | 7/1994 | Mantelle et al. | |
| 5,446,070 A | 8/1995 | Mantelle | |
| 5,613,958 A * | 3/1997 | Kochinke | A61K 9/7084 424/449 |
| 5,719,197 A | 2/1998 | Kanios et al. | |
| 5,958,446 A | 9/1999 | Miranda et al. | |
| 6,024,974 A | 2/2000 | Li | |
| 6,024,976 A | 2/2000 | Miranda et al. | |
| 6,210,705 B1 | 4/2001 | Mantelle et al. | |
| 6,235,306 B1 | 5/2001 | Miranda et al. | |
| 6,316,022 B1 | 11/2001 | Mantelle et al. | |
| 6,348,211 B1 | 2/2002 | Mantelle et al. | |
| 7,063,859 B1 * | 6/2006 | Kanios | A61K 9/7053 424/448 |
| 7,846,916 B2 | 12/2010 | Houze | |
| 7,867,986 B2 | 1/2011 | Houze | |
| 7,879,831 B2 | 2/2011 | Houze | |
| 7,989,496 B2 | 8/2011 | Hartwig et al. | |
| 7,993,671 B2 | 8/2011 | Mantelle et al. | |
| 8,153,151 B2 | 4/2012 | Houze | |
| 8,187,628 B2 | 5/2012 | Houze | |
| 8,216,606 B2 | 7/2012 | Houze | |
| 8,231,906 B2 | 7/2012 | Mantelle | |
| 8,246,976 B2 | 8/2012 | Nguyen | |
| 8,277,838 B2 | 10/2012 | Nguyen | |
| 8,337,884 B2 | 12/2012 | Mantelle et al. | |
| 8,343,538 B2 | 1/2013 | Kanios et al. | |
| 8,632,802 B2 | 1/2014 | Kanios | |
| 8,703,175 B2 | 4/2014 | Kanios et al. | |
| 8,715,723 B2 | 5/2014 | Kanios et al. | |
| 8,784,874 B2 | 7/2014 | Strauss | |
| 8,784,877 B2 | 7/2014 | Houze et al. | |
| 8,871,245 B2 | 10/2014 | Hiraoka et al. | |
| 2005/0208116 A1 | 9/2005 | Stefano et al. | |
| 2007/0098771 A1 * | 5/2007 | Audett | A61K 9/7061 424/449 |
| 2007/0128263 A1 * | 6/2007 | Gargiulo | A61K 9/7084 424/449 |
| 2009/0060986 A1 * | 3/2009 | Yum | A61K 9/7053 424/448 |
| 2010/0087768 A1 | 4/2010 | Forlano et al. | |
| 2011/0129535 A1 | 6/2011 | Mantelle | |
| 2011/0160245 A1 | 6/2011 | Mantelle et al. | |
| 2011/0288124 A1 | 11/2011 | Mantelle et al. | |
| 2013/0156815 A1 | 6/2013 | Mantelle | |
| 2013/0317461 A1 | 11/2013 | Kanios et al. | |
| 2013/0324575 A1 | 12/2013 | Mantelle et al. | |
| 2014/0105979 A1 | 4/2014 | Liao et al. | |
| 2014/0121611 A1 | 5/2014 | Lambert et al. | |
| 2014/0179739 A1 | 6/2014 | Mantelle et al. | |
| 2014/0182597 A1 | 7/2014 | Patel et al. | |
| 2014/0186424 A1 | 7/2014 | Kulakofsky et al. | |
| 2014/0188056 A1 | 7/2014 | Mori et al. | |
| 2014/0200530 A1 | 7/2014 | Mantelle | |
| 2014/0243764 A1 | 8/2014 | Kanios et al. | |
| 2014/0248330 A1 | 9/2014 | Kanios | |
| 2014/0271792 A1 | 9/2014 | Liao et al. | |
| 2014/0271865 A1 | 9/2014 | Lambert et al. | |
| 2014/0276479 A1 | 9/2014 | Nguyen et al. | |
| 2014/0276483 A1 | 9/2014 | Liao et al. | |
| 2014/0288038 A1 | 9/2014 | Kanios et al. | |
| 2014/0336253 A1 | 11/2014 | Breitenbach et al. | |
| 2016/0030362 A1 * | 2/2016 | Liao | A61K 9/7084 424/448 |

FOREIGN PATENT DOCUMENTS

WO WO2013/072062 * 5/2013 .............. A61K 9/70

OTHER PUBLICATIONS

Duro-Tak and Gelva Transdermal Pressure Sensitive Adhesives Product Selection Guide (2013).*

(Continued)

*Primary Examiner* — Sean M Basquill
(74) *Attorney, Agent, or Firm* — Foley & Lardner LLP

(57) ABSTRACT

Described are transdermal drug delivery systems for the transdermal administration of tertiary amine drugs, such as rivastigmine, fentanyl or rotigotine, comprising a polymer matrix comprising a free base form of the drug and at least one carboxyl group-containing compound. In some embodiments, the systems include a rate-controlling membrane and a skin-contacting face adhesive apart from the polymer matrix.

32 Claims, 9 Drawing Sheets

(56) References Cited

OTHER PUBLICATIONS

Rajesh Vadlapatia, et al, Drug-Organic Electrolyte Complexes as Controlled Release Systems, 35 Drug Dev. Indust. Pharm. 1 (2009).*
Agnes L.F. Chan, et al, Transdermal Delivery of Treatment for Alzheimer's Disease, 25 Drugs Aging 761 (Year: 2008).*
U.S. Appl. No. 14/208,367, filed Mar. 13, 2014, Nguyen et al.
U.S. Appl. No. 13/616,919, filed Sep. 14, 2012, Houze et al.
U.S. Appl. No. 14/208,348, filed Mar. 13, 2014, Liao et al.
International Search Report dated Jul. 23, 2014 in application No. PCT/US2014/025845.

* cited by examiner

COMPOSITIONS AND METHODS FOR TRANSDERMAL DELIVERY OF TERTIARY AMINE DRUGS

CROSS-REFERENCE TO RELATED APPLICATIONS

This application claims the priority benefits of U.S. provisional patent application 61/793,120, filed Mar. 15, 2013, the entire contents of which are incorporated herein by reference.

FIELD OF THE INVENTION

Described herein are transdermal drug delivery systems and methods for the transdermal delivery of tertiary amine drugs. In specific embodiments, the transdermal drug delivery systems and methods are useful for extended drug delivery, such as drug delivery over a period of time of 3 days, 7 days, or longer.

BACKGROUND

This invention relates generally to transdermal drug delivery systems, and more particularly, to transdermal drug delivery systems for the delivery of tertiary amine drugs (such as rivastigmine, fentanyl or rotigotine). The use of a transdermal drug delivery system, for example, a patch comprising a pressure-sensitive adhesive containing a drug, as a means of delivering drug through the skin is well known. However, there remains a need for transdermal drug delivery systems designed for the delivery of specific classes of drugs, such as tertiary amine drugs, including rivastigmine, fentanyl and rotigotine, and there remains a need for transdermal drug delivery systems that can provide drug delivery over an extended period of time, such as over a period of time of 3 days, or 7 days, or longer.

Transdermal drug delivery systems (adhesive patches) as dosage forms have been the subject of a vast number of patent applications over the last 25 years, yielding many patents but few commercial products in comparison. To those working in the field, the relatively small number of commercial products is not surprising. Although regulatory, economic, and market hurdles play a role in limiting the number of products on the market, the task of developing a transdermal drug delivery system that achieves desired physical and pharmacokinetic parameters to satisfy physician and patient demand is more daunting. Parameters to be considered during commercial product development may include drug solubility, drug stability (e.g., as may arise from interaction with other component materials and/or the environment), delivery of a therapeutic amount of drug at a desired delivery rate over the intended duration of use, adequate adhesion at the anatomical site of application, integrity (e.g., minimal curling, wrinkling, delaminating and slippage) with minimal discomfort, irritation and sensitization both during use and during and after removal, and minimal residual adhesive (or other components) after removal. The physical manufacturing and production aspects of commercial product development (e.g., the identity and costs of materials, equipment, and labor) and supporting analytical methods required for regulatory compliance also can be significant.

Rivastigmine is a parasympathomimetic or cholinergic agent approved for the treatment of mild to moderate dementia of the Alzheimer's type and dementia due to Parkinson's disease. The drug can be administered orally or transdermally. The commercially available transdermal rivastigmine product (Exelon®) is designed for daily use and comprises four layers: a backing layer, a polymer-drug matrix layer, and adhesive layer and a release liner. The Exelon® patch is available in two sizes, a 5 cm$^2$ patch that includes 9 mg rivastigmine and delivers about 4.6 mg rivastigmine in 24 hours, and a 10 cm$^2$ patch that includes 18 mg rivastigmine and delivers about 9.5 mg in 24 hours rivastigmine. (The 10 cm$^2$ patch that provides a close of 9.5 mg/24 hours is the recommended effective dose.)

Rotigotine is used to treat Parkinson's disease (PD) and restless legs syndrome (RLS). Current 1-day patch products deliver 1, 2, 3, 4, 6 and 8 mg/day of rotigotine for the treatment of Parkinson's disease or restless legs syndrome.

Fentanyl is used to treat pain. Current 3-day patch products deliver 12.5, 25, 50, 75 and 100 μg/hr of fentanyl for pain management.

There remains a need for transdermal drug delivery systems and methods for the transdermal delivery of tertiary amine drugs, such as rivastigmine, rotigotine and fentanyl, and there remains a particular need for transdermal drug delivery systems and methods useful for extended drug delivery, such as drug delivery over a period of time of 3 days, 7 days, or longer.

SUMMARY

In accordance with some embodiments, there are provided transdermal drug delivery systems comprising a polymer matrix comprising the free base form of a tertiary amine drug and at least one carboxyl group-containing compound, wherein the relative amounts of free base and carboxyl group-containing compound is such that greater than 50%, such as at least 60% at least 70%, at least 80%, at least 90%, or 100%, of the free base is associated with a carboxylic acid group to form a salt. In some embodiments, at least one carboxyl group-containing compound is a carrier polymer comprising carboxy-functional groups, such as an acrylic pressure-sensitive adhesive polymer comprising carboxy-functional groups, and/or is a polymeric carboxylic acid, such as anionic copolymers based on methacrylic acid and methyl methacrylate, carbomer polymers, carbopol polymers, vinyl polymers containing carboxylic acid groups, carboxyl group-containing cellulose polymers and carboxyl group-containing starches.

In any embodiments, the tertiary amine drug is selected from the group consisting of amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, fentanyl, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, rivastigmine, rotogotine, scopolamine, telenzepine, theophylline, tolterodine, trimipramine, trihexyphenidyl, tropatepine, and tropicamide.rivastigmine.

In some embodiments, the composition does not include a penetration enhancer comprising a carboxylic acid group. In some embodiments, the composition does not include a monocarboxylic fatty acid.

In any embodiments, the polymer matrix may further comprise an antioxidant and/or.a plasticizer.

In specific embodiments, a transdermal drug delivery system for the transdermal delivery of a tertiary amine drug comprises a polymer matrix comprising:

about 10% to about 40% by weight of a free base form of the tertiary amine drug;

about 0% to about 90% by weight of a carrier polymer, optionally containing carboxyl-group containing carboxy-functional groups;

about 0% to about 90% by weight of a carboxyl group-containing compound;

optionally, about 0% to about 1% of an antioxidant; and optionally, about 0% to about 20% of a pharmaceutically acceptable excipient, wherein the relative amounts of free base and carboxyl groups is such that greater than 50% of the free base is associated with a carboxylic acid group to form a salt.

In accordance with any embodiments, the polymer matrix may comprise an amount of tertiary amine drug effective to deliver a therapeutically effective amount of tertiary amine drug over a period of time selected from the group consisting of at least 1 day, at least 2 days, at least 3 days, at least 4 days, at least 5 days, at least 6 days and at least 7 days.

In accordance with any embodiments where the tertiary amine drug is rivastigmine, the polymer matrix may comprise an amount of rivastigmine effective to deliver at least about 4.6 mg/day over a period of time selected from the group consisting of at least 1 day, at least 2 days, at least 3 days, at least 4 days, at least 5 days, at least 6 days and at least 7 days, or may comprise an amount of rivastigmine effective to deliver at least about 9.5 mg/day over a period of time selected from the group consisting of at least 1 day, at least 2 days, at least 3 days, at least 4 days, at least 5 days, at least 6 days and at least 7 days, or may comprise about 32-65 mg rivastigmine, or may comprise about 67-126 mg rivastigmine.

In accordance with any embodiments, the polymer matrix may have a coat weight of about 10-15 mg/cm$^2$.

Also provided are methods of making a transdermal drug delivery system for a tertiary amine drug, comprising forming a polymer matrix comprising a free base form of the tertiary amine drug and at least one carboxyl group-containing compound, wherein the relative amounts of free base and carboxyl group-containing compound is such that greater than 50% of the free base is associated with a carboxylic acid group to form a salt.

Also provided are transdermal drug delivery systems comprising a polymer matrix comprising the free base form of a tertiary amine drug, a rate-controlling membrane, and a face adhesive comprising a carboxyl group-containing compound. In accordance with these embodiments, the tertiary amine drug and carboxyl group-containing compound may be any as noted above and discussed herein below. In some embodiments, the rate-controlling membrane comprises a polymer selected from the group consisting of polyethylene, polyolefin, and/or ethylene vinyl acetate polymers. In some embodiments, the polymer matrix comprises a polymer selected from the group consisting of acrylic polymers, silicon polymers, polyisobutylene polymers, styrene-isoprene styrene block copolymers, and mixtures of two or more thereof. In some embodiments, the face adhesive comprises a polymer selected from the group consisting of acrylic polymers, silicon polymers, and mixtures of two or more thereof. In accordance with these embodiments, the amount of drug and pharmacokinetic properties may be any as noted above and discussed herein below.

Also provided are methods of making a transdermal drug delivery system for a tertiary amine drug, comprising combining a polymer matrix comprising a free base form of the tertiary amine drug; a rate-controlling membrane; and a face adhesive comprising a carboxyl group-containing compound.

Also provided are methods for administering a tertiary amine drug, comprising applying to the skin or mucosa of a subject in need thereof a transdermal drug delivery system as described herein. Also provided are transdermal drug delivery system as described herein for use in administering a tertiary amine drug to the skin or mucosa of a subject in need thereof, or for treating mild to moderate dementia of the Alzheimer's type or dementia due to Parkinson's disease (for rivastigmine products), Parkinson's disease (PD) or restless legs syndrome (RLS) (for rotigotine products), or pain (for fentanyl products). Also provided are uses of a tertiary amine drug in the preparation of the medicament in form of a the transdermal drug delivery systems as described herein for administering a tertiary amine drug to the skin or mucosa of a subject in need thereof, or for treating mild to moderate dementia of the Alzheimer's type or dementia due to Parkinson's disease (for rivastigmine products), Parkinson's disease (PD) or restless legs syndrome (RLS) (for rotigotine products), or pain (for fentanyl products).

DETAILED DESCRIPTION

Figure 1:
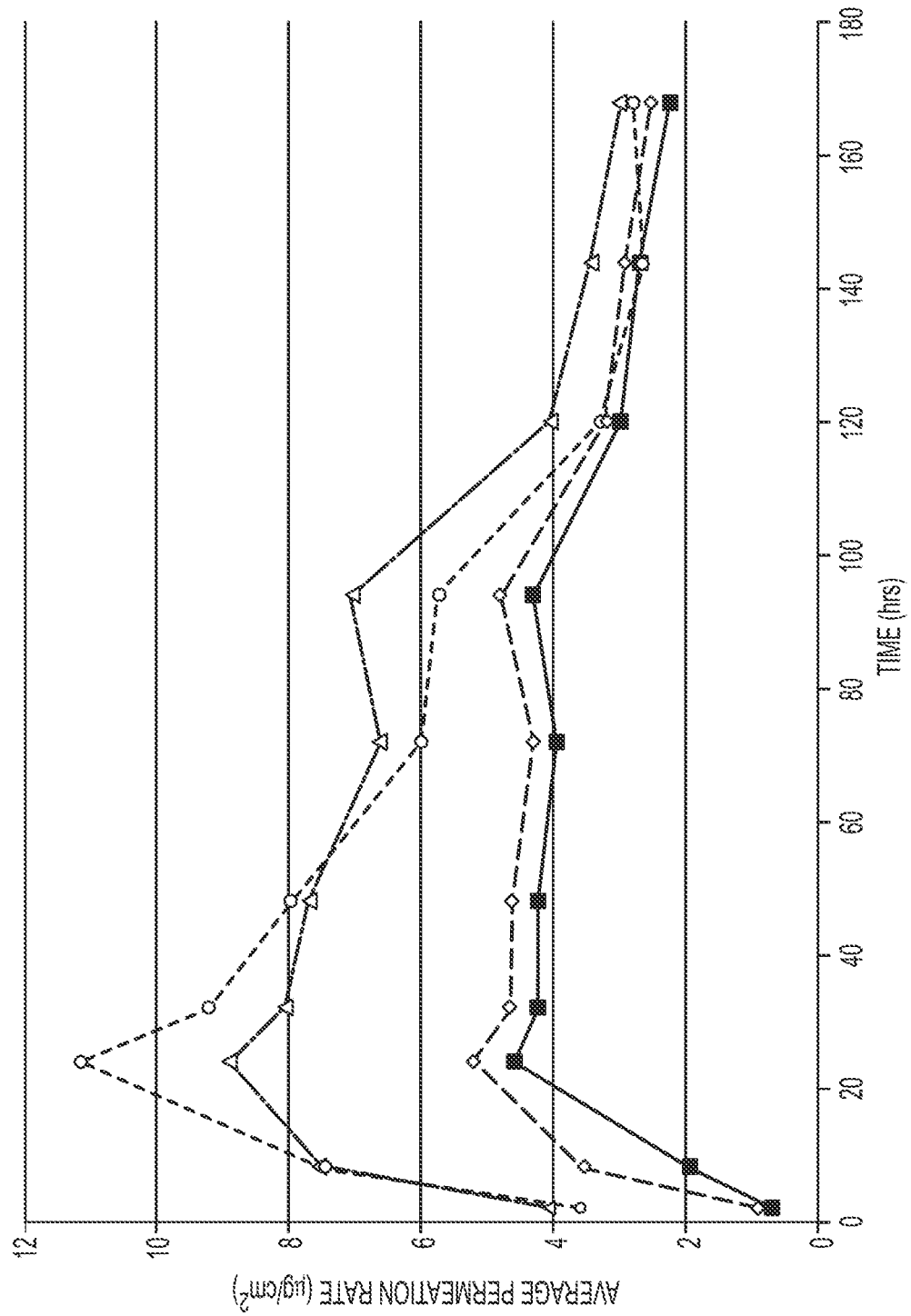
FIG. 1 illustrates the rivastigmine flux ($\mu$g/cm$^2$/hr) over time (0-168 hours) from a transdermal drug delivery system comprising Composition 1-1 (♦), Composition 1-2 (■), Composition 1-3 (▲), or an Exelon® patch (●, top line).

Described herein are transdermal drug delivery systems and methods for the transdermal delivery of tertiary amine drugs, such as rivastigmine, fentanyl or rotigotine. In specific embodiments, the systems achieve delivery of the drug over an extended time period, such a period of greater than one day, such as a period of at least 3 days, at least 5 days, at least 7 days, or longer. In specific embodiments, the systems comprise a tertiary amine drug and a carboxyl group-containing compound in the same layer of the transdermal drug delivery system and/or in different layers.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described composition (e.g., transdermal drug delivery system, polymer matrix, etc.) comprises less than about 5%, less than about 3%, or less than about 1% by weight, based on the total weight of the composition or layer at issue, of the excluded component.

As used herein "subject" denotes any animal in need of drug therapy, including humans. For example, a subject may be suffering from or at risk of developing a condition that can be treated or prevented with a tertiary amine drug (such as rivastigmine, fentanyl or rotigotine), or may be taking a tertiary amine drug (such as rivastigmine fentanyl or rotigotine) for health maintenance or other purposes.

As used herein, the phrases "therapeutically effective amount" and "therapeutic level" mean that drug dosage or plasma concentration in a subject, respectively, that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing layer or skin-contacting face adhesive layer of the transdermal drug delivery system.

As used herein, "coat weight" refers to the weight of the drug-containing layer per unit area of the active surface area of the transdermal drug delivery system.

As used herein, "rivastigmine" includes rivastigmine free base, which is a liquid drug with a tertiary amine structure. The chemical name of rivastigmine is (S)-3-[1-(dimethylamino)ethyl]phenyl ethylmethylcarbamate, its empirical formula is $C_{14}H_{22}N_2O_2$ and its molecular weight is 250.34.

As used herein, "tertiary amine drug" includes any therapeutically active compound with a tertiary amine structure, including amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, fentanyl, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, rivastigmine, rotogotine, scopolamine, telenzepine, theophylline, tolterodine, trimipramine, trihexyphenidyl, tropatepine, and tropicamide.

As used herein, "flux" (also called "permeation rate") is defined as the absorption of a drug through skin or mucosal tissue, and is described by Fick's first law of diffusion:

$$J = -D(dCm/dx)$$

where J is the flux in $g/cm^2/sec$, D is the diffusion coefficient of the drug through the skin or mucosa in $cm^2/sec$ and dCm/dx is the concentration gradient of the drug across the skin or mucosa.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases drug upon application to the skin (or any other surface noted above). A transdermal drug delivery system may comprise a drug-containing layer, and, optionally, a backing layer and/or a release liner layer. In some embodiments, the transdermal drug delivery system comprises a skin-contacting face adhesive layer, a rate-controlling membrane and a drug-containing layer, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject.

As described below, in some embodiments, the transdermal drug delivery system comprises a drug-containing polymer matrix that comprises a pressure-sensitive adhesive or bioadhesive, and is adopted for direct application to a user's (e.g., a subject's) skin. In other embodiments, transdermal drug delivery system comprises a skin-contacting face adhesive layer separate from the drug-containing polymer matrix. In such embodiments, the polymer matrix optionally may be non-adhesive.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se. A polymer that does not itself functions as an adhesive can be made to do so by the addition of tackifiers, plasticizers, crosslinking agents or other additives.

In some embodiments, the polymer matrix comprises a pressure-sensitive adhesive polymer or a bioadhesive polymer, with drug dissolved or dispersed therein. In some embodiments the polymer matrix comprises a polymer that may or may not be a pressure-sensitive adhesive polymer, and also comprises tackifiers, plasticizers, crosslinking agents, enhancers, co-solvents, tillers, antioxidants, solubilizers, crystallization inhibitors, or other additives described herein. U.S. Pat. No. 6,024,976 describes non-limiting examples of polymer blends that can be used in the transdermal drug delivery systems described herein. The entire contents of U.S. Pat. No. 6,024,976 is incorporated herein by reference.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive within the meaning of the term as used herein if it has the properties of a pressure-sensitive adhesive per se. Other polymers can be made to function as a pressure-sensitive adhesive by admixture with tackifiers, plasticizers or other additives.

The term pressure-sensitive adhesive also includes mixtures of different polymers and mixtures of polymers, such as polyisobutylenes (PIB), of different molecular weights, wherein each resultant mixture is a pressure-sensitive adhesive. In the last case, the polymers of lower molecular weight in the mixture are not considered to be "tackifiers," said term being reserved for additives which differ other than in molecular weight from the polymers, to which they are added.

In some embodiments, the polymer matrix and/or face adhesive is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In some embodiments, the polymer matrix and/or face adhesive has a glass transition temperature ($T_g$), measured using a differential scanning calorimeter, of between about −70° C. and 0° C.

As used herein, the term "rubber-based pressure-sensitive adhesive" refers to a viscoelastic material which has the properties of a pressure-sensitive adhesive and which contains at least one natural or synthetic elastomeric polymer.

In some embodiments, the transdermal drug delivery system includes one or more additional layers, such as one or more additional polymer matrix layers, one or more adhesive layers that adhere the transdermal drug delivery system to the user's skin, such as an adhesive overlay, and/or one or more rate-controlling membrane. In other embodiments, the transdermal drug delivery system is monolithic, meaning that it comprises a single polymer matrix layer comprising a pressure-sensitive adhesive or bioadhesive with drug dissolved or dispersed therein, and no rate-controlling membrane. Thus, as used herein, a "monolithic" transdermal drug delivery system may include a backing layer and/or release liner, and may be provided in a package.

The transdermal drug delivery system also may include a drug impermeable backing layer or film. (By "impermeable" to the drug is meant that no substantial amount of drug loss through the backing layer is observed.) In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's Scotch Pak™ 1012 or 9732 backing material (a polyester film with an ethylene vinyl acetate copolymer heat seal layer) is useful in the transdermal drug delivery systems described herein.

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-Off® 7610 (both silicone-based), Loparex's silicone-coated PET release iner films and 3M's Scotchpak™ 1020, 1022, 9741, 9742, 9744, 9748 and 9755 (fluoropolymer coated polyester films).

The transdermal drug delivery system may be packaged or provided in a package, such as a pouchstock material used in the prior art for transdermal drug delivery systems in general or for transdermal drug delivery systems for the specific tertiary amine drug being formulated (e.g., rivastigmine, fentanyl or rotigotine). For example, DuPont's Surlyn® can be used in a pouchstock material.

As noted above, in specific embodiments, the transdermal drug delivery systems described herein achieve drug delivery over an extended time period, such a period of greater than one day, such as a period of at least 3 days, at least 5 days, at least 7 days, or longer. One challenge encountered in developing transdermal drug delivery systems that can achieve drug delivery over an extended time period relates to the difficulty of achieving stable, sustained-delivery of a therapeutically effective amount of drug.

For example, tertiary amine drugs (such as rivastigmine, fentanyl or rotigotine) permeate across the skin relatively easily through passive pathways. When such drugs are formulated in a polymer matrix, delivery of the drug generally is controlled by diffusion of the drug across the skin, which is highly dependent on the concentration of the drug in the matrix. Thus, the flux of the drug tends to drop significantly over time as the concentration of the drug in the matrix decreases. The transdermal drug delivery systems described herein address this problem by providing one or more additional mechanisms of controlling drug delivery.

It was surprisingly discovered that by providing tertiary amine drugs in a transdermal drug delivery system with a carboxyl group-containing compound, such as a carboxyl group-containing acid excipient or acidifying agent and/or a polymer comprising carboxyl functional groups, the delivery of the tertiary amine drug from the composition can be controlled. For example, carboxyl group-containing compounds present in the transdermal drug delivery system may interact and react with the free base form of the tertiary amine drug to form a salt. However, while not wanting to be bound by any theory, it is believed that only the free base form of tertiary amine drugs are available for permeation across the skin. Thus, when a tertiary amine drug is provided in a transdermal drug delivery system with a carboxyl group-containing compound, the amount of free base available for transdermal delivery will depend on dissociation from the salt form, which in turn is regulated by the association/dissociation equilibrium between the free base and its carboxylic acid salt forms. Thus, again while not wanting to be bound by any theory, it is believed that the salt present in the system provides a constant source of free base that fluxes out of the system and penetrates the skin, thereby permitting sustained, controlled delivery of a pharmaceutically effective amount of drug. In some embodiments, the carboxyl group-containing compound is present in the drug-containing polymer matrix. In other embodiments, the carboxyl group-containing compound is additionally or alternatively present in a separate layer, such as in a skin-contacting face adhesive layer.

Thus, in accordance with some embodiments, the transdermal drug delivery system comprises a drug-containing polymer matrix layer that comprises a tertiary amine drug (such as rivastigmine, fentanyl or rotigotine) in a salt form with a carboxyl group-containing compound, such as a carboxyl group-containing acid excipient or acidifying agent, or a polymer comprising carboxyl functional groups. In specific embodiments, the systems comprise a polymer matrix comprising the free base form of a tertiary amine drug (such as rivastigmine, fentanyl or rotigotine) and a carboxyl group-containing compound. In specific embodiments, the systems comprise a tertiary amine drug in free base form and in a salt form with a carboxyl group-containing compound. In some embodiments, the polymer matrix comprises a carboxyl group-containing polymer, such as a pressure-sensitive adhesive polymer comprising carboxy-functional groups. In some embodiments, the polymer matrix additionally or alternatively comprises a carboxyl group-containing acidifying agent.

In specific embodiments, the compositions comprise a polymer matrix comprising about 10% to about 40% by weight of the free base; about 0% to about 90% by weight of a carrier polymer; about 0% to about 90% by weight of a carboxyl group-containing compound (such as a polymer comprising carboxylic acid groups); about 0% to about 1% of an antioxidant; and about 0% to about 20% of other optional excipients (such as a plasticizer or filler). In specific embodiments, the ratio of the acid and base components are adjusted stoichiometrically such that greater than 50% of the free base is associated with a carboxylic acid to form a salt. In some embodiments, the salt form comprises about at least about 60%, at least about 70%, at least about 80%, or at least about 90%, or more, including about 100%, of the total tertiary amine drug content. In accordance with some embodiments, the content of the salt form is adjusted with reference to the intended application period (e.g., 3 days, 7 days, etc.) in order to achieve the desired drug delivery profile.

In accordance with other embodiments, the transdermal drug delivery system comprises a drug-containing polymer matrix layer that comprises a tertiary amine drug (such as rivastigmine, fentanyl or rotigotine) in free base form (and, optionally, in a salt form with a with a carboxyl group-containing compound) and a face adhesive layer comprising a carboxyl group-containing compound, such as a carboxyl group-containing acid excipient or acidifying agent, or a polymer comprising carboxyl functional groups. In specific embodiments, the face adhesive comprises a carboxyl group-containing polymer, such as a pressure-sensitive adhesive polymer comprising carboxy-functional groups. In some embodiments, the face adhesive additionally or alternatively comprises a carboxyl group-containing acidifying agent.

In some embodiments, the face adhesive includes an amount of carboxyl group-containing compound to form a salt with at least about 60%, at least about 70%, at least about 80%, or at least about 90%, or more, including about 100%, of the tertiary amine drug present in the system (e.g., formulated in the polymer matrix layer). In accordance with some embodiments, the content of the carboxyl group-containing compound is adjusted with reference to the intended application period (e.g., 3 days, 7 days, etc.) in order to achieve the desired drug delivery profile.

In some embodiments, both the polymer matrix and the face adhesive include carboxyl group-containing compounds. In specific embodiments, the total amount of carboxyl group-containing compound present in the polymer matrix and face adhesive is sufficient to form a salt with at least about 60%, at least about 70%, at least about 80%, or at least about 90%, or more, including about 100%, of the tertiary amine drug present in the system (e.g., formulated in the polymer matrix layer). In accordance with some embodiments, the content of the carboxyl group-containing compound is adjusted with reference to the intended application period (e.g., 3 days, 7 days, etc.) in order to achieve the desired drug delivery profile.

Carrier Polymers

The carrier polymer of the polymer matrix may be any polymer suitable for use in a transdermal drug delivery system. In specific embodiments, the carrier polymer is chemically compatible with the tertiary amine drug. For example, the carrier polymer may be a hydrophilic polymer approved for pharmaceutical use such as an acrylic polymer, cellulose polymer, or mixture thereof. In some embodiments, the carrier polymer is a pressure-sensitive adhesive, such as an acrylic pressure-sensitive adhesive, such as those exemplified below. In some embodiments, the carrier polymer includes carboxyl functional groups. In those embodiments, the carrier polymer may function as a carboxyl group-containing compound, as discussed above. For example, a carrier polymer, such as an acrylic pressure-sensitive adhesive polymer, may include carboxyl functional groups which can react via ionic interactions with the tertiary amine groups of the drug to form a salt. In such embodiments, the polymer matrix may require less or none of a separate carboxyl group-containing compound (such as an acidifying agent) which may result in a polymer matrix with better adhesive properties than a matrix that comprises a substantial amount of, for example, an acidifying agent.

As noted above, the carrier polymer may comprise from about 0 to about 90% by weight of the polymer matrix.

Acrylic Polymers

In some embodiments, the polymer carrier comprises an acrylic polymer. The term "acrylic polymer" is used here as in the art interchangeably with "polyacrylate," "polyacrylic polymer," and "acrylic adhesive." The acrylic-based polymers can be any of the homopolymers, copolymers, terpolymers, and the like of various acrylic acids or esters. In some embodiments, the acrylic-based polymers are adhesive polymers. In other embodiments, the acrylic-based polymers function as an adhesive by the addition of tackifiers, plasticizers, crosslinking agents or other additives.

The acrylic polymer can include copolymers, terpolymers and multipolymers. For example, the acrylic polymer can be any of the homopolymers, copolymers, terpolymers, and the like of various acrylic acids. In some embodiments, the acrylic polymer constitutes from about 2% to about 95% by weight of the polymer content of the polymer matrix, including about 3% to about 90% and about 5% to about 85%, such as 2% to 95%, 3% to 90% and 5% to 85%. In some embodiments, the amount and type of acrylic polymer is dependent on the type and amount of tertiary amine drug (such as rivastigmine, fentanyl or rotigotine) used.

Acrylic polymers useful in practicing the invention include polymers of one or more monomers of acrylic acids and other copolymerizable monomers. The acrylic polymers also include copolymers of alkyl acrylates and/or methacrylates and/or copolymerizable secondary monomers or monomers with functional groups. Combinations of acrylic-based polymers based on their functional groups is also contemplated. Acrylic-based polymers having functional groups include copolymers and terpolymers which contain, in addition to nonfunctional monomer units, further monomer units having free functional groups. The monomers can be monofunctional or polyfunctional. By varying the amount of each type of monomer added, the cohesive properties of the resulting acrylic polymer can be changed as is known in the art. In some embodiments, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid and methacrylic acid and alkyl acrylic or methacrylic esters such as methyl acrylate, ethyl acrylate, propyl acrylate, amyl acrylate, butyl acrylate, butyl methacrylate, hexyl acrylate, methyl methacrylate, hexyl methacrylate, heptyl acrylate, octyl acrylate, nonyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, glycidyl acrylate, and corresponding methacrylic esters.

Non-functional acrylic-based polymers can include any acrylic based polymer having no or substantially no free functional groups.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethyl acrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

As used herein, "functional monomers or groups," are monomer units typically in acrylic-based polymers which have reactive chemical groups which modify the acrylic-based polymers directly or which provide sites for further reactions. Examples of functional groups include carboxyl, epoxy, hydroxyl, sulfoxyl, and amino groups. Acrylic-based polymers having functional groups contain, in addition to the nonfunctional monomer units described above, further monomer units having free functional groups. The monomers can be monofunctional or polyfunctional. These functional groups include carboxyl groups, hydroxy groups, amino groups, amino groups, epoxy groups, etc. Typical carboxyl functional monomers include acrylic acid, methacrylic acid, itaconic acid, maleic acid, and crotonic acid. Typical hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. As noted above, in some embodiments, the acrylic polymer does not include such functional groups.

Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989); "Acrylic and Methacrylic Ester Polymers," *Polymer Science and Engineering*, Vol. 1, 2nd ed., pp 234-268, John Wiley & Sons, (1984); U.S. Pat. Nos. 4,390,520; and 4,994,267, all of which are expressly incorporated by reference in their entireties.

Suitable acrylic polymers also include pressure-sensitive adhesives which are commercially available, such as the acrylic-based adhesives sold by Henkel North America under the Duro-Tak® trade name (such as Duro-Tak® 87-2287, -4098, -2852, -2196, -2296, -2194, -2825, -2516, -2070, -2353, -2154, -2510, -4852, -9085, -9088, -9900, -2051, -2052, -2054, 235A, -2074, -2979, -2525, -2677, -4287, -502A, -503A, -504A, -900A, -901A and -9301) and those sold by Cytec Surface Specialties, St. Louis, Mo., under the GELVA® GMS trade name (such as GELVA® GMS 2480, 788, 7883, 737, 263, 1430, 1753, 1151, 2450, 2495, 2499, 3067, 3071, 3083, 3087, 3235, 9073 and 9083). Other suitable acrylic adhesives include those sold under the trademark EUDRAGIT® by Evonik Industries AG, Essen, Germany, For example, hydroxy functional adhesives with a reactive functional OH group in the polymeric chain, can be used. Non-limiting commercial examples of this type of adhesives include both GELVA® GMS 737, 788, and 1151, and Duro-Tak® (DT) 87-2287, -4287, -2510 and -2516.

As noted above, in specific embodiments polymers comprising carboxyl functional groups are used. Non-limiting commercial examples of such polymers include Duro-Tak® 87-2194, -2196, -2852, -2074, -2677, -4852 and GELVA® GMS 9083 and 9073.

Silicon Polymers

In some embodiments, the polymer carrier comprises a silicone-based polymer. The term "silicone-based" polymer is used interchangeably with the terms silicon polymers, siloxane, polysiloxane, and silicones as used herein and as known in the art. A suitable silicone-based polymer may also be a pressure-sensitive adhesive. Thus, in some embodiments, the silicone-based polymer is an adhesive polymer. In other embodiments, the silicone-based polymer functions as an adhesive by the addition of tackifiers, plasticizers, crosslinking agents, or other additives.

Suitable polysiloxanes include silicone pressure-sensitive adhesives which are based on two major components: (i) a polymer or gum and (ii) a tackifying resin. A polysiloxane adhesive can be prepared by cross-linking a gum, typically a high molecular weight polydiorganosiloxane, with a resin, to produce a three-dimensional silicate structure, via a condensation reaction in an appropriate organic, volatile solvent, such as ethyl acetate or heptane. The ratio of resin to polymer can be adjusted in order to modify the physical properties of polysiloxane adhesives. Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989).

Exemplary silicone-based polymers are adhesives (e.g., capable of sticking to the site of topical application), including pressure-sensitive adhesives. Illustrative examples of silicone-based polymers having reduced silanol concentrations include silicone-based adhesives (and capped polysiloxane adhesives) such as those described in U.S. Pat. No. Re. 35,474 and U.S. Pat. No. 6,337,086, which are incorporated herein by reference in their entireties, and which are commercially available from Dow Corning Corporation (Dow Corning Corporation, Medical Products, Midland, Mich.) as BIO-PSA® 7-4100, -4200 and -4300 product series, and non-sensitizing, pressure-sensitive adhesives produced with compatible organic volatile solvents (such as ethyl acetate or heptane) and available commercially under their BIO-PSA® 7-4400 series, -4500 series, such as -4502, and -4600 series.

Further details and examples of silicone pressure-sensitive adhesives which are useful in the polymer matrices and compositions and methods described herein are mentioned in the following U.S. Pat. Nos. 4,591,622; 4,584,355; 4,585,836; and 4,655,767, which are all expressly incorporated by reference herein in their entireties. It should also be understood that silicone fluids are also contemplated for use in the polymer matrices and methods described herein.

In some embodiments, the polysiloxane constitutes from about 9% to about 97% of the polymer content of the polymer matrix, including about 8% to about 97% and about 14% to about 94%, such as 9% to 97%, 8% to 97%, and 14% to 94%.

Other Polymers

As noted above, in some embodiments the polymer matrix comprises one or more rubber-based polymers, such as one or more rubber-based pressure-sensitive adhesives, such as natural or synthetic polyisoprene, polybutylene, polyisobutylene, styrene-butadiene polymers, styrene-isoprene-styrene block copolymers (such as Kraton® D111 KT), hydrocarbon polymers, such as butyl rubber, halogen-containing polymers, such as polyacrylic-nitrile, polytetrafluoroethylene, polyvinylchloride, polyvinylidene chloride, and polychlorodiene, and other copolymers thereof. Additionally or alternatively, as discussed above, the polymer matrix may comprise a non-adhesive polymer, such as ethyl cellulose.

As noted above, the carrier polymer may comprise from about 0 to about 90% by weight of the polymer matrix depending on the target content of the salt form.

Face Adhesive

In some embodiments, the transdermal drug delivery system comprise a skin-contacting face adhesive layer separate from the polymer matrix. In accordance with such embodiments, the face adhesive may comprise any one or more of the polymers described above. In specific embodiments, the face adhesive comprises a silicone polymer, such as one or more of those described above. In other embodiments, the face adhesive comprises an acrylic polymer, such as a non-functional acrylic polymer, including one or more of Duro-Tak® 87-9900, -900A, or GELVA® GMS 3235.

In some embodiments, the polymer component(s) of the face adhesive are selected to achieve one or more of the following characteristics: good skin adhesion for the intended period of application (e.g., at least 1 day, at least 3 days, at least 7 days, or longer); minimal resistance to drug diffusion; minimal solubility for the drug without exhibiting "dumping" upon initial contact with skin that leads to a "burst effect;" physical and chemical compatibility with the drug. As discussed above, including a carboxyl group-containing compound in the face adhesive supports the latter characteristic.

Carboxyl Group-Containing Compounds

In some embodiments, the polymer matrix and/or face adhesive layer includes a carboxyl group-containing compound, such as a carboxyl group-containing acid excipient or acidifying agent, or a polymer comprising carboxyl functional groups.

Polymers

As noted above, in some embodiments the carrier polymer and/or face adhesive includes carboxyl functional groups. In such embodiments, the polymer may function as a carboxyl group-containing compound. For example, a carrier polymer or face adhesive polymer, such as an acrylic pressure-sensitive adhesive polymer, may include carboxyl functional groups which can react via ionic interactions with the tertiary amine groups of the tertiary amine drug (such as rivastigmine, fentanyl or rotigotine) to form a salt. In such embodiments, the polymer matrix or face adhesive layer may require less or none of a separate carboxyl group-containing compound (such as an acidifying agent) which may result in a polymer matrix or face adhesive with better adhesive properties than a matrix that comprises a substantial amount of, for example, an acidifying agent.

Suitable polymers that include carboxyl functional groups include the carboxy-functional acrylic polymers illustrated above. Specific examples of such a polymer include Duro-Tak® 87-2852, 87-4852, and 87-2194. In embodiments where the carboxyl group-containing compound is provided in a separate layer from the polymer matrix, such as in a face adhesive layer, the separate layer (e.g., the face adhesive layer) may include any of these carboxy-functional acrylic polymers.

Acidifying Agents

As noted above, in some embodiments the carboxyl group-containing compound is provided as a carboxyl group-containing acid excipient or acidifying agent. In specific embodiments, the carboxyl group-containing compound is a carboxylic acid, such as a polymeric carboxylic acid. In specific embodiments, the carboxylic acid is one that will not diffuse out of the patch into the skin. In specific embodiments, the carboxylic acid is a polymer excipient containing carboxyl groups, such as Eudragit® L 100 or Eudragitt® S 100 polymers (anionic copolymers based on methacrylic acid and methyl methacrylate in a 1:1 or 1:2 ratio, respectively) and carbomer or carbopol polymers (e.g., synthetic high molecular weight crosslinked polymers of acrylic acid), other vinyl polymers containing carboxylic acid groups, and carboxyl-containing cellulose or starch, such as carboxymethyl cellulose or starch. In other embodiments the acidifying agent is an acid, such as lactic acid, oleic acid, and the like.

In some embodiments the carboxyl group-containing compound is not itself a penetration enhancer, such as a fatty acid known for use as a penetration enhancer, such as oleic acid. Thus, in some embodiments, the transdermal drug delivery system does not include a penetration enhancer that includes a carboxylic acid group.

In some embodiments the carboxyl group-containing compound is not a monocarboxylic fatty acid, such as capric acid or lauric acid, or a bile acid, such as a monocarboxylic fatty acid derived from bile, such as glycocholic acid, glycodeoxycholic acid, cholic acid, deoxycholic acid, taurocholic acid, or taurodexycholic acid. Thus, in some embodiments, the transdermal drug delivery system does not include a monocarboxylic fatty acid, such as any of these monocarboxylic fatty acids.

As noted above, the carboxyl group-containing compound may be provided in the polymer matrix and/or in a separate layer from the polymer matrix, such as in a face adhesive layer. In such embodiments, the separate layer (e.g., the face adhesive layer) may include any of these carboxy-functional acrylic polymers.

Antioxidant

In accordance with any of the embodiments described herein, the polymer matrix and/or face adhesive layer may comprise an antioxidant. In specific embodiments the antioxidant may be one known for use in transdermal drug delivery systems, such as butylhydroxytoluene (BHT), butylhydroxyanisole (BHA), tertiary-butylhydroquinone (TBHQ), ascorbic acid, ascorbyl palmitate, alpha-tocopherol and its esters, fumaric acid, malic acid, sodium ascorbate, sodium metabisulfite, and propyl gallate, and mixtures thereof. As noted above, the antioxidant may comprise from about 0 to about 1%, including from about 0 to about 0.5% by weight of the polymer matrix.

Other Components

In accordance with any of the embodiments described herein, the polymer matrix and/or face adhesive polymer may comprise one or more other pharmaceutically acceptable excipients, such as a plasticizer, penetration enhancer, filler, and the like. In some embodiments, the polymer matrix comprises from about 0% to about 20% of one or more such excipients.

A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In some embodiments, the polymer matrix or transdermal drug delivery system does not include a penetration enhancer. In some embodiments, the polymer matrix or transdermal drug delivery system does not include a penetration enhancer that includes carboxylic acid groups. Thus, in some embodiments, the polymer matrix or or transdermal drug delivery system does not include a penetration enhancer that includes carboxylic acid groups.

The polymer matrix and/or face adhesive may further comprise various thickeners, fillers, and other additives or components known for use in transdermal drug delivery systems to further modify properties of the matrix or face adhesive, such as polyvinylpyrrolidone (PVP), ethylene-vinyl acetate copolymers, cellulose derivatives, $SiO_2$, and other components.

In some embodiments, the polymer matrix or transdermal drug delivery system does not include cyclodextrin, or a complex comprising cyclodextrin and the active agent. Thus, in some embodiments, the polymer matrix or transdermal drug delivery system does not include cyclodextrin, or a complex comprising cyclodextrin and the active agent.

Tertiary Amine Drug

As noted above, as used herein, "tertiary amine drug" includes any therapeutically active compound with a tertiary amine structure, including amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, fentanyl, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, rivastigmine, rotogotine, scopolamine, telenzepine, theophylline, tolterodine, trimipramine, trihexyphenidyl, tropatepine, and tropicamide. In some embodiments, the tertiary amine drug is rivastigmine, rotogotine, or fentanyl.

The amount of tertiary amine drug to be incorporated in the polymer matrix varies depending on the specific drug, the desired therapeutic effect, and the length of time for which the system is to provide therapy. As noted above, in some embodiments, the composition is designed to achieve drug delivery over an extended time period, such a period of greater than one day, such as a period of at least 3 days, at least 4 days, at least 5 days, at least 6 days, at least 7 days, or longer. Thus, in one embodiment, the composition comprises an amount of tertiary amine drug sufficient to deliver therapeutically effective amounts of drug over a period of from 1 day to 3 days, 7 days, or longer, including for 1 day, for 2 days, for 3 days, for 4 days, for 5 days, for 6 days, for 7 days, or for longer.

In embodiments where the tertiary amine drug is rivastigmine, a therapeutically effective amount of rivastigmine delivered by the composition may be from about 3 to about 12 mg/day, including about 4.6 mg/day and about 9.5 mg/day. Thus, in some embodiments, the transdermal drug delivery system comprises an amount of rivastigmine effective to achieve a delivery of from about 3 to about 12 mg/day, including about 4.6 mg/day or about 9.5 mg/day.

In embodiments where the tertiary amine drug is rotogotine, a therapeutically effective amount of rotogotine delivered by the composition may be 1, 2, 3, 4, 6 or 8 mg/day of rotogotine, such as for the treatment of Parkinson's disease or restless legs syndrome.

In embodiments where the tertiary amine drug is fentanyl, a therapeutically effective amount of fentanyl delivered by the composition may be 12.5, 25, 50, 75 or 100 μg/hr of fentanyl, such as for pain management.

As noted above, in some embodiments, therapeutically effective drug delivery rates are sustained over a duration of application of at least about 1 day, including at least about 3 days and at least about 7 days, such as at least 1 day, at least 2 days, at least 3 days, at least 4 days, at least 5 days, at least 6 days, and at least 7 days.

As noted above, in specific embodiments, the ratio of the acid components (e.g., the carboxyl group-containing components) and base components (e.g., rivastigmine free base) are adjusted stoichiometrically such that greater than 50% of the free base is associated with a carboxylic acid to form a salt. In some embodiments, the salt form comprises about at least about 60%, at least about 70%, at least about 80%, or at least about 90%, or more, including about 100%, of the total tertiary amine drug content (e.g., rivastigmine, fentanyl or rotigotine content), including at least 60%, at least 70%, at least 80%, at least 90% and 100%.

Transdermal Drug Delivery Systems

As noted above, the carrier polymer may or may not be a pressure sensitive adhesive. Further, as noted above, the transdermal drug delivery system may be a monolithic device comprised of the polymer matrix, or may include one or more additional layers, such as a face adhesive layer, or may be provided with a surrounding adhesive portion. As noted above, the transdermal drug delivery system may include a backing layer on one side of the polymer matrix layer and a release liner on the other side of the polymer matrix layer. In multilayer systems, the polymer matrix layer may be the skin-contacting layer (e.g., directly adjacent the release liner) or may be separated from the skin by one or more intervening layers, and may or may not be directly adjacent the backing layer. As noted above, an optional overlay adhesive film may be used to strengthen the adhesion of the patch to the skin.

Monolithic Systems

In some embodiments, the system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

Rate-Controlling Membrane

As noted above, in some embodiments, the transdermal drug delivery system includes a rate-controlling membrane disposed between the polymer matrix and the skin-contacting face adhesive. Rate-controlling membranes are known in the art. For example, a rate-controlling membrane may comprise polyethylene, polyolefin, and/or ethylene vinyl acetate, or other polymer films. Exemplary commercial available films suitable for use as rate-controlling membranes include 3M CoTran™ polyethylene/vinyl acetate films, such as CoTran™ 9719 (polyethylene) (1.7 mil), CoTran™ 9720 (polyethylene) (3 mil), CoTran™ 9722 (polyethylene) (3 mil), CoTran™ 9718 (polyethylene) (3.6 mil), CoTran™ 9726 (2% vinyl acetate, 2 mil), CoTran™ 9707 (4.5% vinyl acetate, 2 mil), CoTran™ 9702 (9% vinyl acetate, 2 mil), CoTran™ 9705 (9% vinyl acetate, 3 mil), CoTran™ 9706 (9% vinyl acetate, 4 mil), CoTran™ 9712 (18.5% vinyl acetate, 2 mil), CoTran™ 9728 (18.5% vinyl acetate, 2 mil), CoTran™ 9715 (18.5% vinyl acetate, 3 mil), CoTran™ 9716 (18.5% vinyl acetate, 4 mil).

Drug permeability through the membrane may be selected and controlled by selecting the polymer components of the membrane, for example, by varying the vinyl acetate content of an ethylene vinyl acetate polymer, and/or by selecting and controlling the density of the membrane, and/or by selecting and controlling the thickness of the membrane, and/or by other means known in the art.

The system may be of any shape or size suitable for transdermal application and of an appropriate sizes for application to deliver the desired dose, such as ranging from about 2 $cm^2$ to about 50 $cm^2$, including about 5 $cm^2$, about 10 $cm^2$, about 20 $cm^2$, about 25 $cm^2$, about 30 $cm^2$, about 35 $cm^2$, about 40 $cm^2$, about 45 $cm^2$, and about 50 $cm^2$.

In specific embodiments relating to rivastigmine, the system is about 16-24 $cm^2$, such as 17.5 $cm^2$, 18 $cm^2$, 19 $cm^2$, or 23.5 $cm^2$ and contains about 60-65 mg rivastigmine per unit dose (including 61.9 mg, 63.9 mg, 64 mg) and/or delivers a dose of about 4.6 mg/day, and about 32.2 mg over 7 days. In other specific embodiments, the system is about 32-48 $cm^2$, such as 35 $cm^2$, 36 $cm^2$, 38 $cm^2$, or 47 $cm^2$, and contains about 126 mg rivastigmine per unit dose and/or delivers a dose of about 9.5 mg/day, and about 66.5 mg over 7 days. In further specific embodiments relating to rivastigmine, the system contains about 32-65 mg rivastigmine per unit dose, or about 67-126 mg rivastigmine per unit dose.

The polymer matrices described herein may be prepared by methods known in the art. For example, a polymer matrix can be prepared by blending the components of the polymer matrix, applying the matrix material to a support layer such as a backing layer or release liner (such as by calender coating, hot melt coating, solution coating, etc.), and removing any remaining solvents. The polymer matrices can be formed into systems by methods known in the art, such as by die-cutting into sizes and shapes suitable for use.

The tertiary amine drug can be added at any stage. In one embodiment, all polymer matrix components, including the drug, are blended together. The order of steps, amount of ingredients, and the amount and time of agitation or mixing can be determined and optimized by the skilled practitioner. An exemplary general method is as follows:

Appropriate amounts of solvent(s), enhancer(s), and organic solvent(s) (for example toluene, or ethyl acetate and/or isopropyl alcohol) are combined and thoroughly mixed together in a vessel.

The tertiary amine drug (such as rivastigmie) and any antioxidant being used (such as BHT) are added to the mixture and agitation is carried out until the drug is uniformly mixed in.

Appropriate amounts of acrylic polymer, carboxyl group-containing compound (e.g., acidifying agent), and other excipients are then added to the drug mixture, and thoroughly mixed.

The formulation is then transferred to a coating operation where it is coated onto a protective release liner at a controlled specified thickness. The coated product is then passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

In some embodiments, the coat weight of the polymer matrix is selected and tailored to control and/or optimize the drug delivery profile. For example, systems with a higher coat weight (e.g., unit weight of polymer matrix per unit area of system) may achieve increased drug flux and improved flux profile.

Therapeutic Methods

In some embodiments, there is provided a method of effecting transdermal drug delivery of a tertiary amine drug, such as rivastigmine, fentanyl or rotigotine, by applying a system as described herein to the skin or mucosa of a subject in need thereof. In some embodiments, the system is applied over a period of at least about 1 day, at least about 2 days, at least about 3 days, at least about 4 days, at least about 5 days, at least about 6 days, or at least about 7 days, such as for 1, 2, 3, 4, 5, 6 or 7 days, or longer. In some embodiments, the method is effective to achieve transdermal delivery of therapeutically effective amounts of drug during the application period. In some embodiments, the method is effective to achieve therapeutic levels of drug in the subject during the application period. In some embodiments, the method is effective to achieve a substantially constant rate of drug delivery over a period of at least about 1 day, at least about 2 days, at least about 3 days, at least about 4 days, at least about 5 days, at least about 6 days, or at least about 7 days, or longer.

As noted above, a typical rivastigmine dosage ranges from at about 3 to about 12 mg/day, including about 4.6 or 9.5 mg/day. In some embodiments, the rivastigmine systems described herein are designed for use by patients suffering from or at risk of developing dementia associated with Alzheimer's disease or Parkinson's disease.

As noted above, a typical rotigotine dosage ranges from about 1 to about 10 mg/day, including 1, 2, 3, 4, 6 or 8 mg/day of rotigotine. In some embodiments, the rotigotine systems described herein are designed for use by patients suffering from or at risk of developing Parkinson's disease or restless legs syndrome.

As noted above, a typical fentanyl dosage ranges from about 10 to about 100 100 µg/hr, including 12.5, 25, 50, 75 or 100 µg/hr of fentanyl. In some embodiments, the fentanyl systems described herein are designed for use by patients suffering from or at risk of developing pain.

The following specific examples are included as illustrative of the transdermal drug delivery systems and polymer matrices described herein. These examples are in no way intended to limit the scope of the invention. Other aspects of the invention will be apparent to those skilled in the art to which the invention pertains.

Example 1

Polymer matrices with the following compositions were prepared:

| Composition | Carboxy-Functional DURO-TAK ® Polymer | Anti-oxidant | Rivastigmine | Target Salt Percentage |
|---|---|---|---|---|
| 1-1 | 87-4852 79% | BHT 1% | 20% | 97% |
| 1-2 | 87-4852 76.5% | BUT 1% | 22.5% | 82% |
| 1-3 | 87-4852 74% | BHT 1% | 25% | 72% |
| 1-6 | 87-2852 79% | BHT 1% | 20% | 97% |
| 1-7 | 87-2852 76.5% | BHT 1% | 22.5% | 82% |
| 1-8 | 87-2852 74% | BHT 1% | 25% | 72% |
| 1-9 | 87-2194 79% | BHT 1% | 20% | 69% |
| 1-10 | 87-2194 76.5% | BHT 1% | 22.5% | 59% |
| 1-11 | 87-2194 74% | BHT 1% | 25% | 51% |
| Exelon ® | 87-2353 70% | | 30% | <49% |

Each polymer matrix is applied with a coat weight of about 10-15 mg/cm$^2$ (e.g., 12.5±2.5 mg/cm$^2$) to a release liner, and a backing material is applied. Human cadaver skin permeation studies are performed to assess permeation through the stratum corneum.

FIG. 1 illustrates the rivastigmine flux (µg/cm$^2$/hr) over time (0-168 hours) from a transdermal drug delivery system comprising Composition 1-1 (♦), Composition 1-2 (■), Composition 1-3 (▲), or an Exelon® patch (●, top line).

Figure 2:
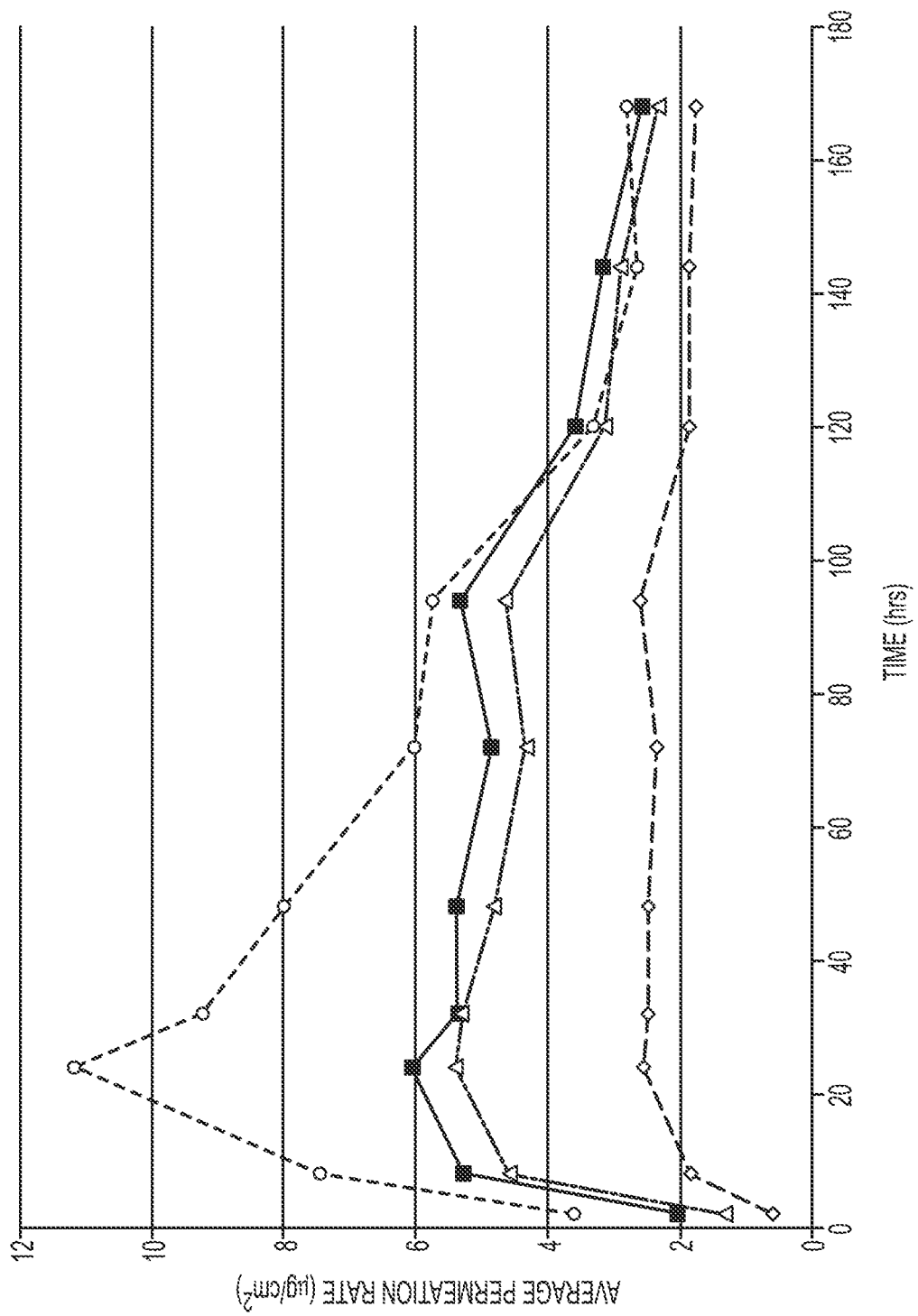
FIG. 2 illustrates the rivastigmine flux ($\mu$g/cm$^2$/hr) over time (0-168 hours) from a transdermal drug delivery system comprising Composition 1-6 (♦), Composition 1-7 (■), Composition 1-8 (▲) or an Exelon® patch (●, top line).

FIG. 2 illustrates the rivastigmine flux (µg/cm$^2$/hr) over time (0-168 hours) from a transdermal drug delivery system comprising Composition 1-6 (♦), Composition 1-7 (■), Composition 1-8 (▲) or an Exelon® patch (●, top line).

Figure 3:
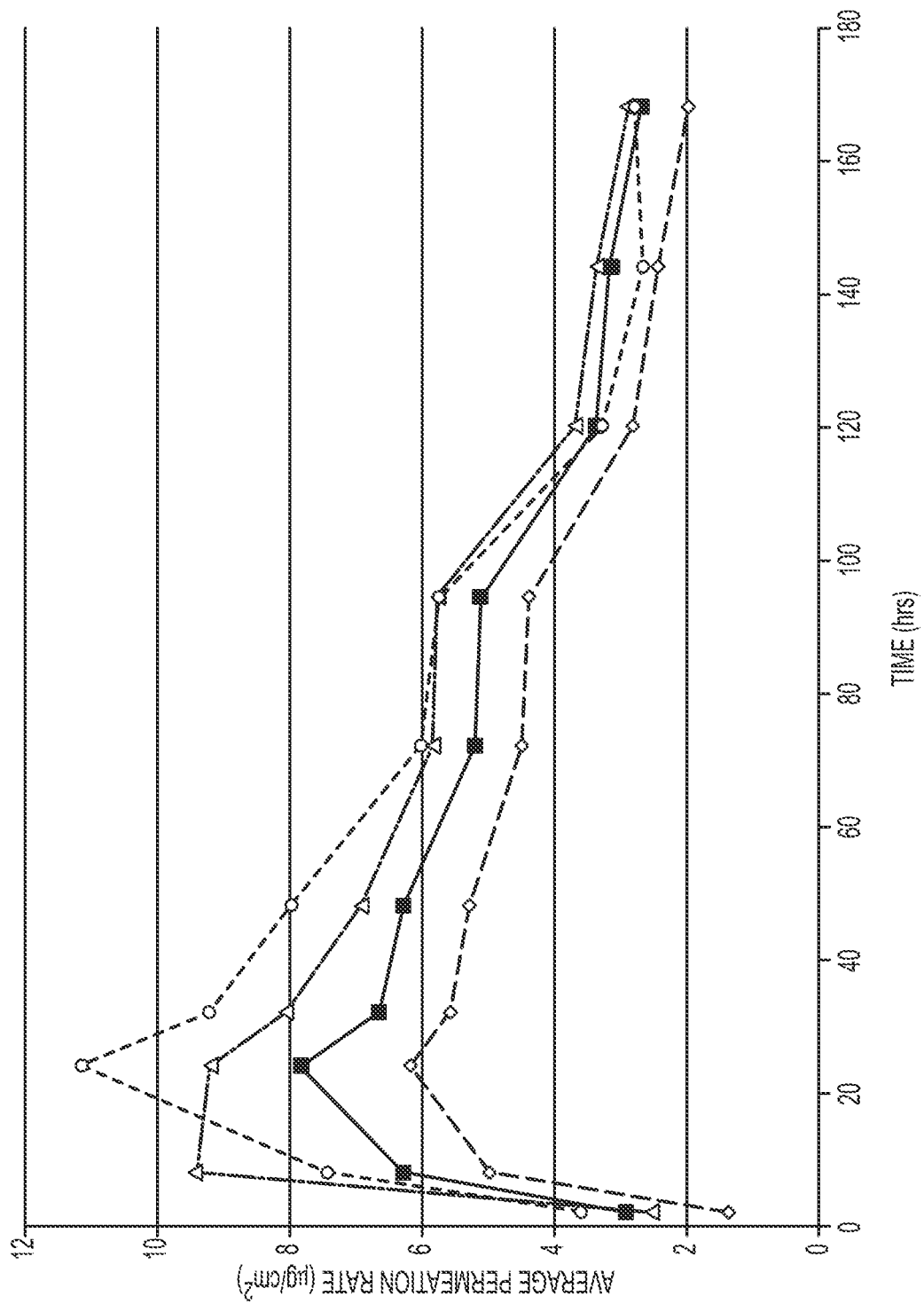
FIG. 3 illustrates the rivastigmine flux ($\mu$g/cm$^2$/hr) over time (0-168 hours) from a transdermal drug delivery system comprising Composition 1-9 (♦), Composition 1-10 (■), Composition 1-11 (▲) or an Exelon® patch (●, top line).

FIG. 3 illustrates the rivastigmine flux (µg/cm$^2$/hr) over time (0-168 hours) from a transdermal drug delivery system comprising Composition 1-9 (♦), Composition 1-10 ■), Composition 1-11 (▲) or an Exelon® patch (●, top line).

The results show that the systems according to the invention achieve sustained, controlled flux over a 7-day application period.

Pharmacokinetic analyses were performed with a transdermal system comprising Composition 1-6 as the polymer matrix layer.

| Composition | Salt (%) | Cmax (24 h) | Cmin (168 h) | Tail Off | Patch Size | Est. Coat Weight |
|---|---|---|---|---|---|---|
| 1-6 | 97 | 2.6 | 1.8 | 31% | 47 cm$^2$ | 13.4 mg/cm$^2$ |
| Exelon ® | <49 | 11.2 | 2.8 | 75% | 10 cm$^2$ | 9 mg/cm$^2$ |

The results show that the system comprising Composition 1-6 as the polymer matrix achieves sustained, controlled drug delivery over a 7-day application period.

Example 2

Polymer matrices with the following compositions were prepared:

| Composition | Carboxy-Functional DURO-TAK ® Polymer | Anti-oxidant | Eudragit ® L100 | Drug | Target Salt Percentage |
|---|---|---|---|---|---|
| 2-1 | 87-2852 69% | BHT 1% | — | 30% | 56% |
| 2-2 | 87-2852 63% | BHT 1% | 6% | 30% | 80% |
| 2-3 | 87-2852 60% | BHT 1% | 9% | 30% | 90% |
| 2-4 | 87-2852 58% | BHT 1% | 11% | 30% | 100% |
| 2-5 | 87-2852 74% | BHT 1% | — | 25% | 72% |
| 2-6 | 87-2852 72.3% | BHT 1% | 1.7% | 25% | 80% |
| 2-7 | 87-2852 70% | BHT 1% | 4% | 25% | 90% |
| 2-8 | 87-2852 68% | BHT 1% | 6% | 25% | 100% |

Each polymer matrix is applied with a coat weight of about 10-15 mg/cm$^2$ (e.g., 12.5±2.5 mg/cm$^2$) to a release liner, and a backing material is applied. Human cadaver skin permeation studies are performed to assess permeation through the stratum corneum.

Figure 4:
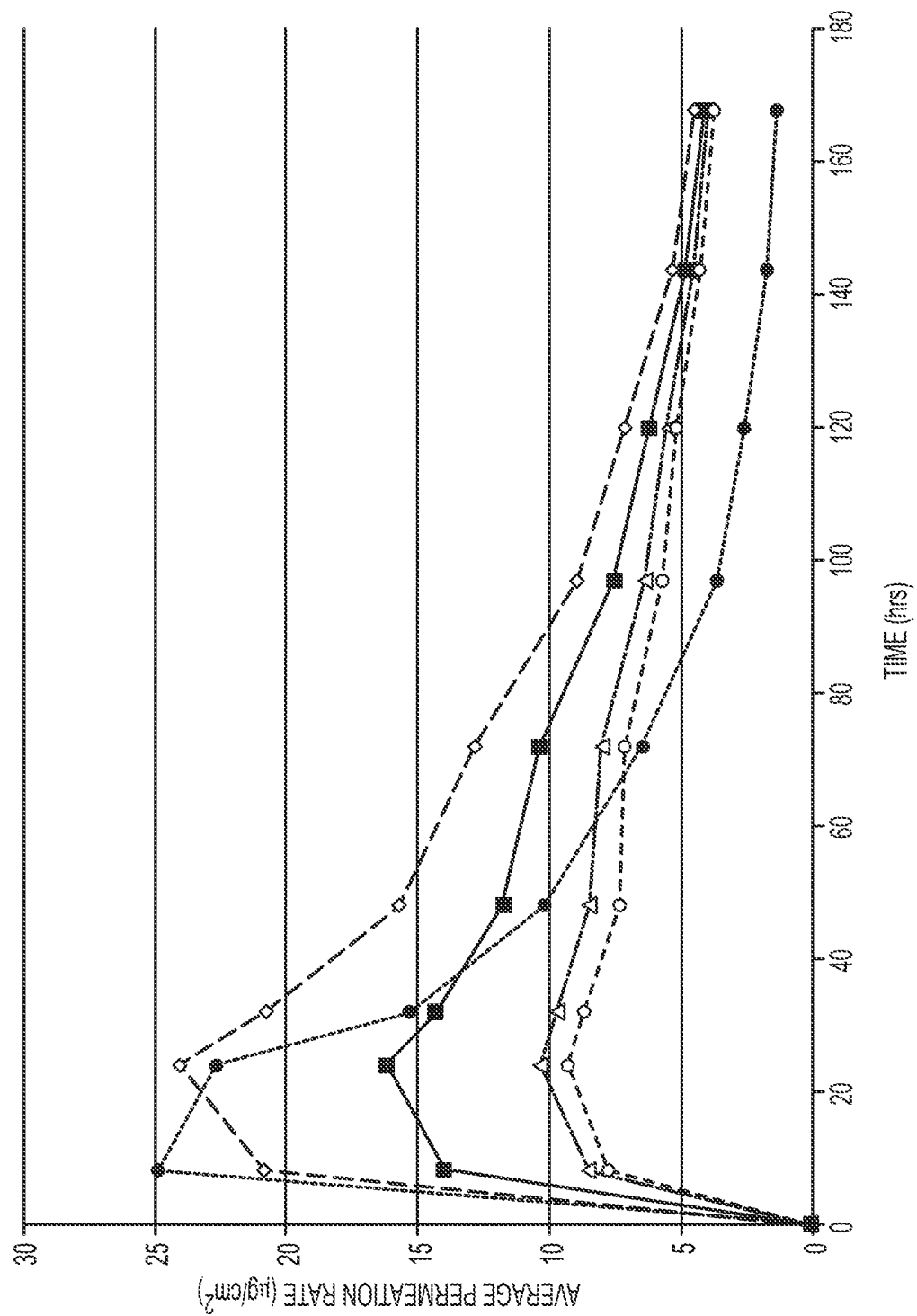
FIG. 4 illustrates the rivastigmine flux ($\mu$g/cm$^2$/hr) over time (0-168 hours) from a transdermal drug delivery system comprising Composition 2-1 (♦), Composition 2-2 (■), Composition 2-3 (▲), Composition 2-4 (O), or an Exelon® patch (●, top line).
Figure 5:
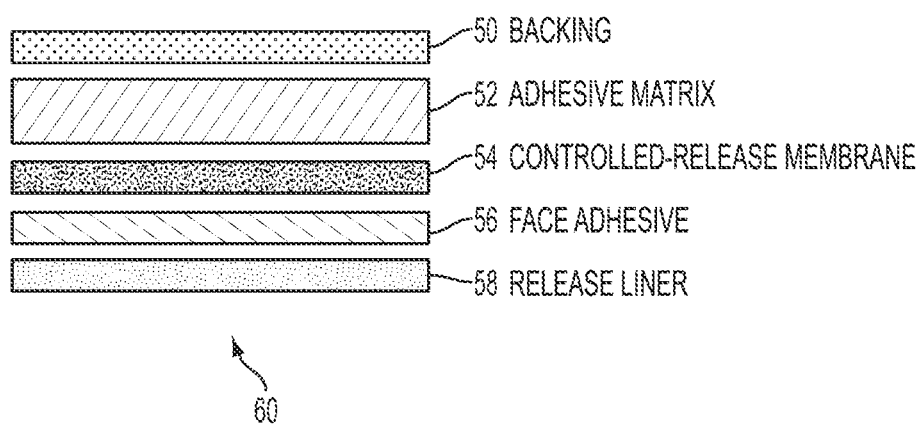
FIG. 5 illustrates a transdermal drug delivery system 60 as described herein comprising a backing 50, an adhesive matrix 52, a rate-controlling membrane 54, a face-adhesive 56, and a release liner 58.

FIG. 4 illustrates the rivastigmine flux (µg/cm$^2$/hr) over time (0-168 hours) from a transdermal drug delivery system comprising Composition 2-1 (♦), Composition 2-2 (■), Composition 2-3 (▲), Composition 2-4 (O), or an Exelon® patch (●, top line).

The results show that the systems according to the invention achieve sustained, controlled flux over a 7-day application period.

Pharmacokinetic analyses were performed with a transdermal system comprising Compositions 2-1 through 2-8 as the polymer matrix layer, applied at a coat weight of about 12.5 mg/cm$^2$ to a release liner and backing layer, using 0.5 cm$^2$ pieces.

| Composition | Salt (%) | Cmax (24 h) | Cmin (168 h) |
|---|---|---|---|
| 2-1 | 56 | 24.1 | 4.4 |
| 2-2 | 80 | 16.2 | 4 |
| 2-3 | 90 | 10.4 | 3.9 |
| 2-4 | 100 | 9.3 | 3.8 |
| 2-5 | 72 | 19.1 | 3.5 |
| 2-6 | 80 | 21.3 | 3.9 |
| 2-7 | 90 | 13.6 | 3.5 |
| 2-8 | 100 | 10.9 | 3.5 |
| Exelon ® | <49 | 24.8 (8 hr) | 1.3 |

The results show that the systems comprising compositions as described herein as the polymer matrix achieve sustained, controlled drug delivery over a 7-day application period.

Example 3

Transdermal drug delivery systems were prepared using Compositions 2-3, 2-4 and 2-8, as follows:

| Composition | Salt (%) | Est. Coat Weight (mg/cm$^2$) | Size (4.6 mg/day)) (cm$^2$) | Size (9.5 mg/day)) (cm$^2$) |
|---|---|---|---|---|
| 2-3 | 90 | 12.2 | 17.5 | 35 |
| 2-4 | 100 | 11.2 | 19 | 38 |
| 2-8 | 100 | 14.2 | 18 | 36 |

These transdermal drug delivery systems are able to achieve sustained, controlled delivery of rivastigmine at pharmaceutically effective amounts over a period of time of at least 7 days.

Example 4

Transdermal drug delivery systems were prepared as follows:

| Layer | Components |
|---|---|
| Backing | Mylar ® M813 |
| Adhesive Matrix (15 mg/cm$^2$) | 30% Rivastigmine<br>69% DURO-TAK ® 87-9900<br>1% BHT |
| Rate-Controlling Membrane | CoTran ™ 9719 (1.7 mil) (System 4-1) (■) or<br>CoTran ™ 9720 (3 mil) (System 4-2) (▲) |
| Face Adhesive (5 mg/cm$^2$) | 97% BIO-PSA ® 4302<br>3% Eudragit ® L100 |
| Release Liner | 3M ScotchPak ® 1022 |

Figure 6:
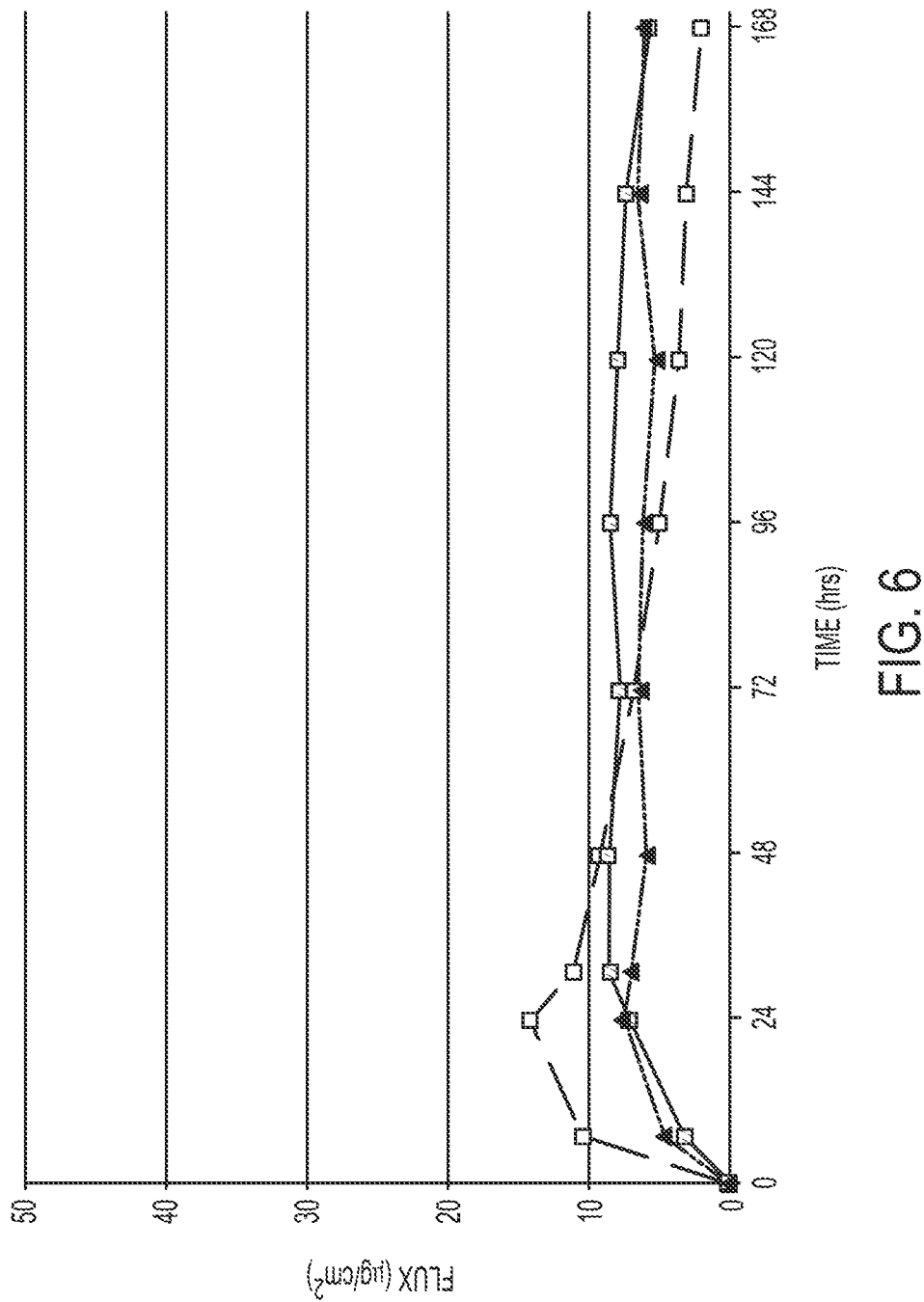
FIGS. 6 and 7 illustrate the rivastigmine flux ($\mu$g/cm$^2$/hr) over time (0-168 hours) from transdermal drug delivery systems described herein (System 4-1 (■); System 4-2 (▲)) or an Exelon® patch (■, top line at 0-48 hours) in an in vitro flux study using human skin.
Figure 7:
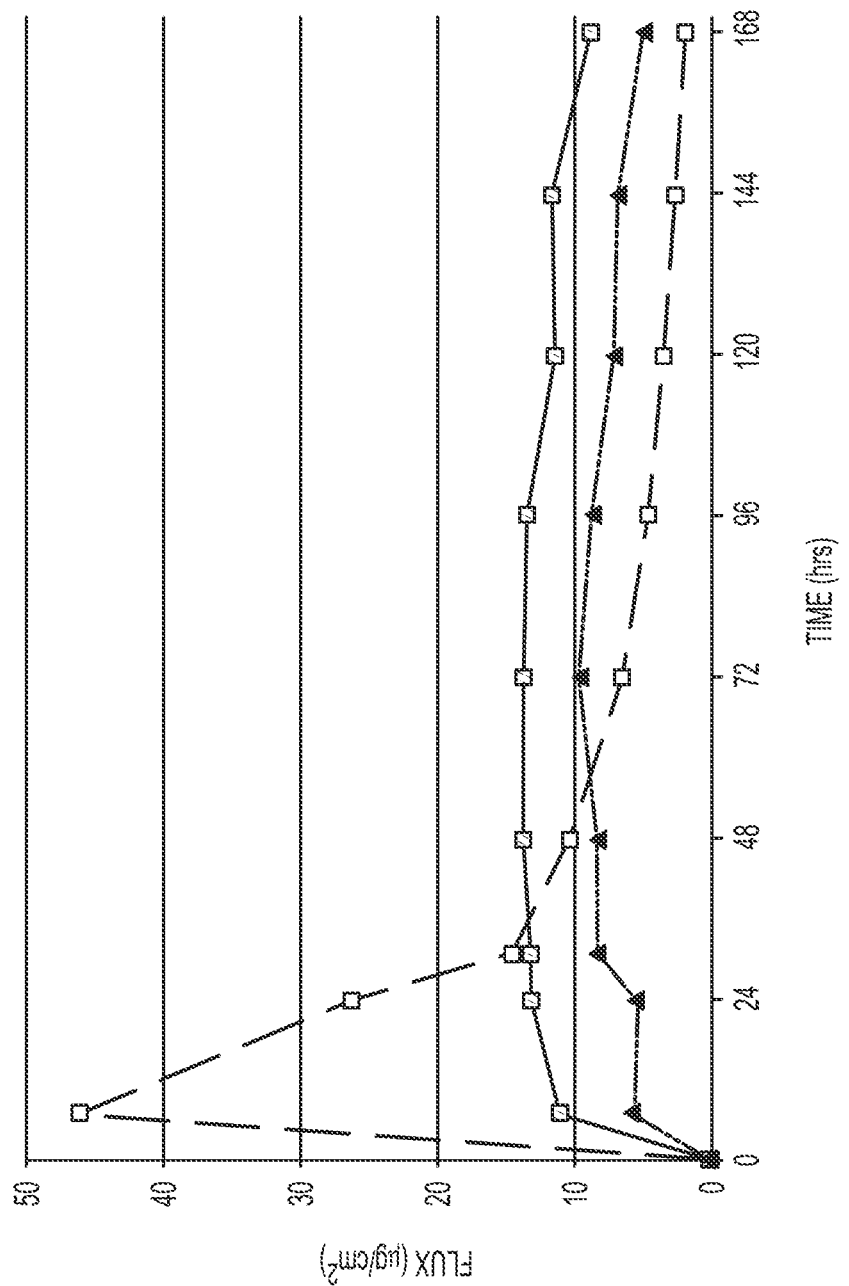

FIGS. 6 and 7 illustrate the rivatsigmine flux (μg/cm$^2$/hr) over time (0-168 hours) from the transdermal drug delivery systems described above (System 4-1 (■): System 4-2 (▲)) or an Exelon® patch (■, top line at 0-48 hours) in an in vitro flux study using human skin from two different donors, respectively. The results show that the systems according to the invention achieve sustained, controlled flux over a 7-day period. Further, the results show that the systems according to the invention exhibited less flux variability and less donor-to-donor variability than the Exelon® patch.

Example 5

The flux of rivatsigmine liquid ("infinite-dose" of 0.5 ml/cm$^2$) across systems prepared using different rate controlling membranes (with different vinyl acetate contents and different thicknesses) with or without a 5 mg/cm$^2$ silicone face adhesive was assessed in an in vitro flux study, as shown below. CoTran™ 9720 (PE 3 mil) exhibited the most rate control. The 5 mg/cm2 silicone face adhesive exhibited a relatively small resistance to drug flux.

| | Rivastigmine steady-state flux (μg/cm$^2$/hr) | | |
|---|---|---|---|
| | CoTran ™ only | CoTran ™ + Silicone face adhesive (5 mg/cm$^2$) | human skin only |
| (human skin) | — | — | 32 ± 14 |
| CoTran ™ 9720 (0% VA) (3 mil) | 11 | 8 | |
| CoTran ™ 9719 (0% VA) (1.7 mil) | 26 | — | |
| CoTran ™ 9726 (2% VA) (2 mil) | 21 | 19 | |
| CoTran ™ 9707 (4.5% VA) (2 mil) | 34 | 24 | |
| CoTran ™ 9702 (9% VA) (2 mil) | 73 | 50 | |
| CoTran ™ 9712 (18.5% VA (2 mil) | 230 | 254 | |

Figure 8:
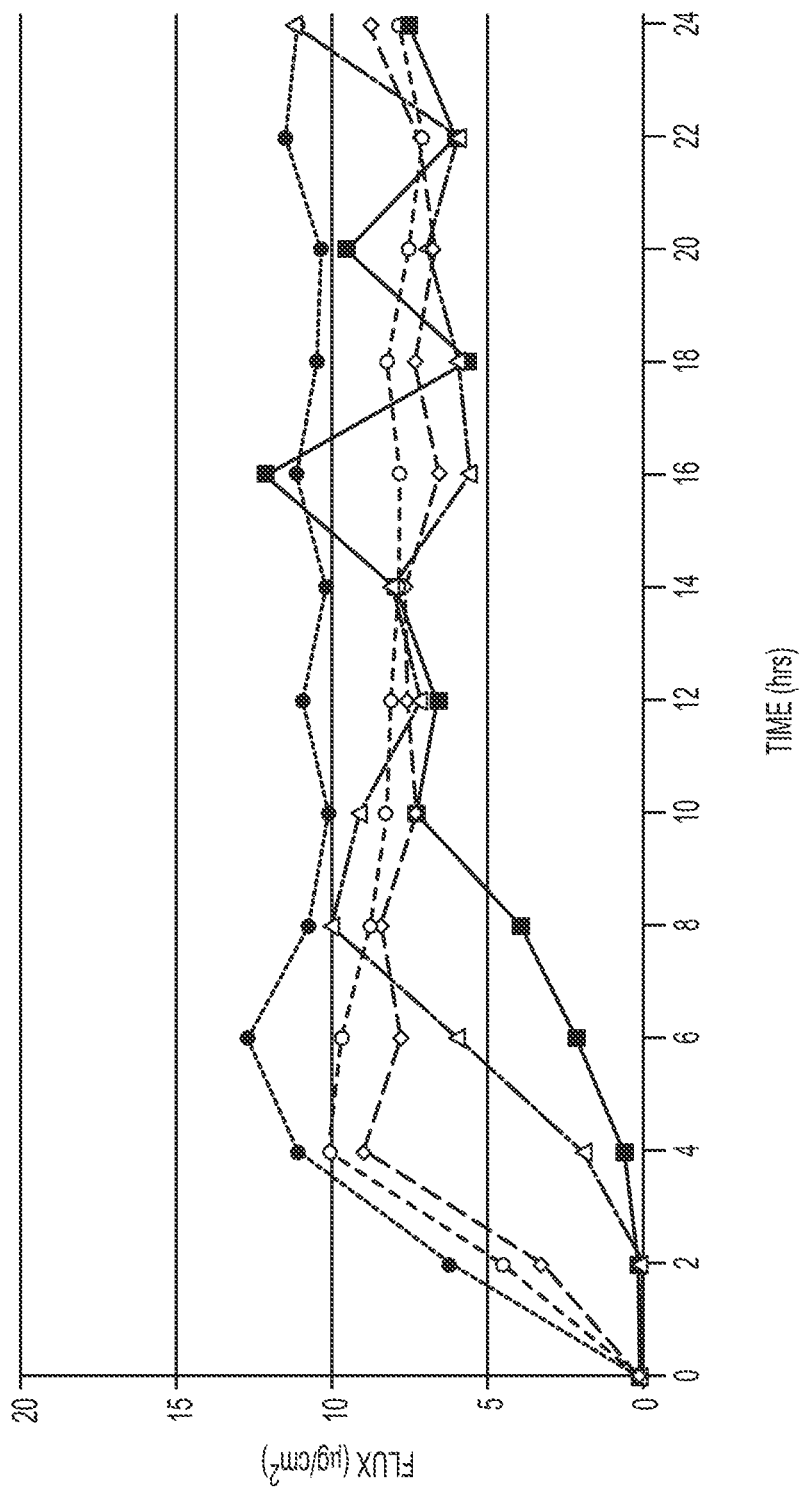
FIG. 8 illustrates the rivastigmine flux ($\mu$g/cm$^2$/hr) over time (0-168 hours) from the transdermal drug delivery systems described herein with a rate-controlling membrane and different face adhesives (5 mg/cm$^2$): none (●); silicone (■); silicone and GELVA® GMS 3235 (▲); silicone and Duro-Tak® 9900 (O); silicone and Duro-Tak® 87-900A (♦).

A similar study was conducted using CoTran™ 9720 with different face adhesives (5 mg/cm$^2$): none (●); silicone (■); silicone and GELVA® GMS 3235 (▲); silicone and Dura-Tak® 9900 (O); silicone and Dura-Tak® 87-900A (♦). Results are shown in FIG. 8. As seen in the figure, the face adhesives exhibited a relatively small resistance to drug flux as compared to the CoTran™ 9720 alone.

Example 6

Transdermal drug delivery systems were prepared using a polymer matrix comprising (on a wt % basis) 30% rivastigmine free base (neat liquid), 69% Duro-Tak® 9900 and 1% BHT, a rate-controlling membrane as set forth below, and a face adhesive comprised of Duro-Tak® 2852.
CoTran™ 9719 (VA 0%) (●)
CoTran™ 9719 (VA 2%) (■)
CoTran™ 9707 (VA 4.5%) (▲)

Figure 9:
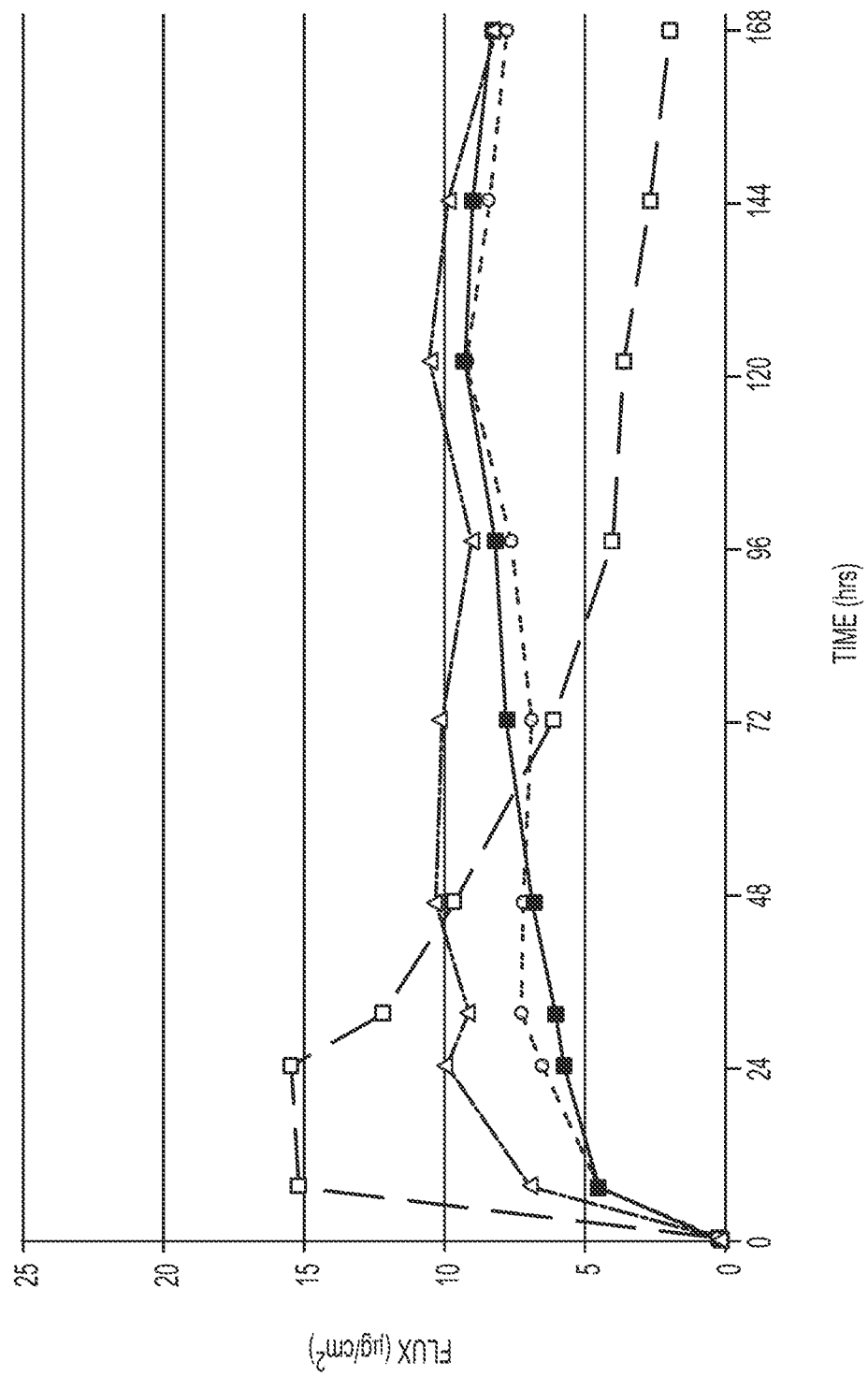
FIG. 9 illustrates the in vitro rivastigmine flux ($\mu$g/cm$^2$/hr) over time (0-168 hours) from transdermal drug delivery systems described herein with different rate-controlling membranes and Duro-Tak® 87-2852 face adhesive, or an Exelon® patch (■, top line at 0-24 hours).

FIG. 9 illustrates the in vitro rivastigmine flux (μg/cm$^2$/hr) over time (0-168 hours) from the transdermal drug delivery systems described above or an Exelon® patch (■, top line at 0-24 hours). The results show that the systems according to the invention achieve sustained, controlled flux over a 7-day application period. Further, the results show that the systems according to the invention exhibited less flux variability then Exelon® patch. The same formulations were used in a 7-day rabbit irritation test and found to be non-irritating or mildly irritating.

What is claimed is:
1. A transdermal drug delivery system comprising:
    a polymer matrix formed by blending the free base form of a tertiary amine drug and at least one carboxyl group-containing compound, wherein the relative amounts of free base and carboxyl group-containing compound is such that greater than 50% of the free base is associated with a carboxylic acid group to form a salt, and
    a backing layer,
    wherein the transdermal drug delivery system releases drug upon application to skin, and is effective to deliver a therapeutically effective amount of the tertiary amine drug through skin for at least 3 days.
2. The transdermal drug delivery system according to claim 1, wherein the relative amounts of free base and carboxyl group-containing compound is such that at least 60% of the free base is associated with a carboxylic acid group to form a salt.

3. The transdermal drug delivery system according to claim 1, wherein the relative amounts of free base and carboxyl group-containing compound is such that at least 70% of the free base is associated with a carboxylic acid group to form a salt.

4. The transdermal drug delivery system according to claim 1, wherein the relative amounts of free base and carboxyl group-containing compound is such that at least 80% of the free base is associated with a carboxylic acid group to form a salt.

5. The transdermal drug delivery system according to claim 1, wherein the relative amounts of free base and carboxyl group-containing compound is such that at least 90% of the free base is associated with a carboxylic acid group to form a salt.

6. The transdermal drug delivery system according to claim 1, wherein the relative amounts of free base and carboxyl group-containing compound is such that about 100% of the free base is associated with a carboxylic acid group to form a salt.

7. The transdermal drug delivery system according to claim 1, wherein at least one carboxyl group-containing compound is a carrier polymer comprising carboxy-functional groups.

8. The transdermal drug delivery system according to claim 1, wherein at least one carboxyl group-containing compound is an acrylic pressure-sensitive adhesive polymer comprising carboxy-functional groups.

9. The transdermal drug delivery system according to claim 1, wherein at least one carboxyl group-containing compound is a polymeric carboxylic acid.

10. The transdermal drug delivery system according to claim 9, wherein the polymeric carboxylic acid is selected from the group consisting of anionic copolymers based on methacrylic acid and methyl methacrylate, carbomer polymers, carbopol polymers, vinyl polymers containing carboxylic acid groups, carboxyl group-containing cellulose polymers and carboxyl group-containing starches.

11. The transdermal drug delivery system according to claim 1, wherein the tertiary amine drug is selected from the group consisting of amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, fentanyl, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, rivastigmine, rotogotine, scopolamine, telenzepine, theophylline, tolterodine, trimipramine, trihexyphenidyl, tropatepine, tropicamide, and rivastigmine.

12. The transdermal drug delivery system according to claim 1, wherein the composition does not include a penetration enhancer comprising a carboxylic acid group.

13. The transdermal drug delivery system according to claim 1, wherein the composition does not include a monocarboxylic fatty acid.

14. The transdermal drug delivery system according to claim 1, wherein the polymer matrix further comprises an antioxidant.

15. The transdermal drug delivery system according to claim 1, wherein the polymer matrix further comprises a plasticizer.

16. The transdermal drug delivery system according to claim 1, wherein the polymer matrix comprises:
   about 10% to about 40% by weight of a free base form of the tertiary amine drug;
   about 0% to about 90% by weight of a carrier polymer, optionally containing carboxyl-group containing carboxy-functional groups;
   about 0% to about 90% by weight of a carboxyl group-containing compound;
   optionally, about 0% to about 1% of an antioxidant; and
   optionally, about 0% to about 20% of a pharmaceutically acceptable excipient,
   wherein the relative amounts of free base and carboxyl groups is such that greater than 50% of the free base is associated with a carboxylic acid group to form a salt.

17. The transdermal drug delivery system according to claim 1, wherein the system is effective to deliver a therapeutically effective amount of tertiary amine drug through skin over a period of time selected from the group consisting of at least 4 days, at least 5 days, at least 6 days and at least 7 days.

18. The transdermal drug delivery system according to claim 1, wherein the tertiary amine drug is rivastigmine and the system is effective to deliver through skin (i) at least about 4.6 mg/day over a period of time selected from the group consisting of at least 3 days, at least 4 days, at least 5 days, at least 6 days and at least 7 days or (ii) at least about 9.5 mg/day over a period of time selected from the group consisting of at least 3 days, at least 4 days, at least 5 days, at least 6 days and at least 7 days.

19. The transdermal drug delivery system according to claim 1, wherein the polymer matrix has a coat weight of about 10-15 mg/cm$^2$.

20. A method for administering a tertiary amine drug, comprising applying to the skin of a subject in need thereof a transdermal drug delivery system according to claim 1.

21. A method of making a transdermal drug delivery system for a tertiary amine drug, comprising:
   forming a polymer matrix by blending a free base form of the tertiary amine drug and at least one carboxyl group-containing compound, wherein the relative amounts of free base and carboxyl group-containing compound is such that greater than 50% of the free base is associated with a carboxylic acid group to form a salt, and
   wherein the transdermal drug delivery system releases drug upon application to skin, and is effective to deliver a therapeutically effective amount of the tertiary amine drug through skin for at least 3 days.

22. A transdermal drug delivery system comprising a polymer matrix comprising the free base form of a tertiary amine drug, a rate-controlling membrane, and a face adhesive comprising a carboxyl group-containing compound, wherein the rate controlling membrane is disposed between the polymer matrix and the face adhesive, and wherein the system is effective to deliver a therapeutically effective amount of the tertiary amine drug through skin for at least 3 days.

23. The transdermal drug delivery system according to claim 22, wherein the rate-controlling membrane comprises a polymer selected from the group consisting of polyethylene, polyolefin, and/or ethylene vinyl acetate polymers.

24. The transdermal drug delivery system according to claim 22, wherein the polymer matrix comprises a polymer selected from the group consisting of acrylic polymers, silicone polymers, polyisobutylene polymers, styrene-isoprene styrene block copolymers, and mixtures of two or more thereof.

25. The transdermal drug delivery system according to claim 22, wherein the face adhesive comprises a polymer selected from the group consisting of acrylic polymers, silicone polymers, and mixtures of two or more thereof.

26. The transdermal drug delivery system according to claim 22, wherein the system is effective to deliver a therapeutically effective amount of tertiary amine drug through skin over a period of time selected from the group consisting of at least 4 days, at least 5 days, at least 6 days and at least 7 days.

27. The transdermal drug delivery system according to claim 22, wherein the tertiary amine drug is rivastigmine and the system is effective to deliver through skin (i) at least about 4.6 mg/day over a period of time selected from the group consisting of at least 3 days, at least 4 days, at least 5 days, at least 6 days and at least 7 days or (ii) at least about 9.5 mg/day over a period of time selected from the group consisting of at least 3 days, at least 4 days, at least 5 days, at least 6 days and at least 7 days.

28. The transdermal drug delivery system according to claim 22, wherein the polymer matrix has a coat weight of about 10-15 mg/cm$^2$.

29. A method for transdermally administering a tertiary amine drug through skin, comprising applying to the skin of a subject in need thereof a transdermal drug delivery system according to claim 22.

30. A method of making a transdermal drug delivery system for a tertiary amine drug, comprising combining
   a polymer matrix comprising a free base form of the tertiary amine drug in an amount effective to deliver a therapeutically effective amount of the tertiary amine drug through skin for at least 3 days;
   a rate-controlling membrane; and
   a face adhesive comprising a carboxyl group-containing compound
   wherein the rate controlling membrane is disposed between the polymer matrix and the face adhesive, and wherein the system is effective to deliver a therapeutically effective amount of the tertiary amine drug through skin for at least 3 days.

31. The transdermal drug delivery system according to claim 1, wherein the tertiary amine drug is rivastigmine and the polymer matrix includes an amount of rivastigmine selected from about 32-65 mg and about 67-126 mg.

32. The transdermal drug delivery system according to claim 22, wherein the tertiary amine drug is rivastigmine and the polymer matrix includes an amount of rivastigmine selected from about 32-65 mg and about 67-126 mg.

* * * * *